United States Patent [19]

Block

[11] 4,293,316
[45] Oct. 6, 1981

[54] INLET SYSTEM FOR A GAS ANALYZER

[75] Inventor: Barry Block, Los Altos Hills, Calif.

[73] Assignee: Harry E. Aine, Los Altos, Calif. ; a part interest

[21] Appl. No.: 838,310

[22] Filed: Sep. 30, 1977

[51] Int. Cl.³ .................... B01D 53/04; B01D 53/22; G01N 5/02
[52] U.S. Cl. .................................. 55/16; 55/18; 55/74; 55/158; 55/179; 55/270; 55/387; 73/23.1
[58] Field of Search ............ 23/230 EP, ; 55/16, 55/74, 158, 179, 208, 387, 18, 270; 73/23.1

[56] References Cited

U.S. PATENT DOCUMENTS

| | | | |
|---|---|---|---|
| 3,430,482 | 3/1969 | Dravnieks et al. | 73/23.1 |
| 3,455,817 | 7/1969 | Modell | 55/16 X |
| 3,568,411 | 3/1971 | Dravnieks et al. | 55/208 |
| 3,638,401 | 2/1972 | Kabler | 55/158 |
| 3,674,435 | 7/1972 | Van Luik, Jr. et al. | 55/16 X |
| 3,772,909 | 11/1973 | Anderson | 73/23.1 |
| 3,976,450 | 8/1976 | Marcote et al. | 55/158 |
| 4,051,372 | 9/1977 | Aine | 55/158 X |

Primary Examiner—Robert H. Spitzer
Attorney, Agent, or Firm—Harry E. Aine; Harvey G. Lowhurst

[57] ABSTRACT

The detector region of a gas analyzer is interfaced to a source of gas under analysis, such as the atmosphere, by means of an adsorber type preconcentrator, which preferentially adsorbs the gaseous constituent of interest, such as relatively heavy hydrocarbons, while permitting the other lighter hydrocarbons, water vapor, and permanent gases to pass thereby without appreciable adsorption. After a substantial volume of gas to be analyzed has passed through the adsorber stage, the adsorbed materials are desorbed from the surface of the adsorber into the input stage of a membrane separator. As a consequence, the partial pressure of the constituent of interest is greatly increased at the input stage of the membrane separator. The gaseous constituent of interest is then passed through the membrane separator, and further separated therein from water vapor, the permanent gases and some of the lighter hydrocarbons and then passed into the detector region of the gas analyzer. In a preferred embodiment, the output stage of the membrane separator is connected to a second adsorber concentrator so that the partial pressure at the output of the membrane separator is reduced for the gaseous constituent of interest so as to facilitate flow of the gaseous constituent of interest through the membrane separator.

13 Claims, 1 Drawing Figure

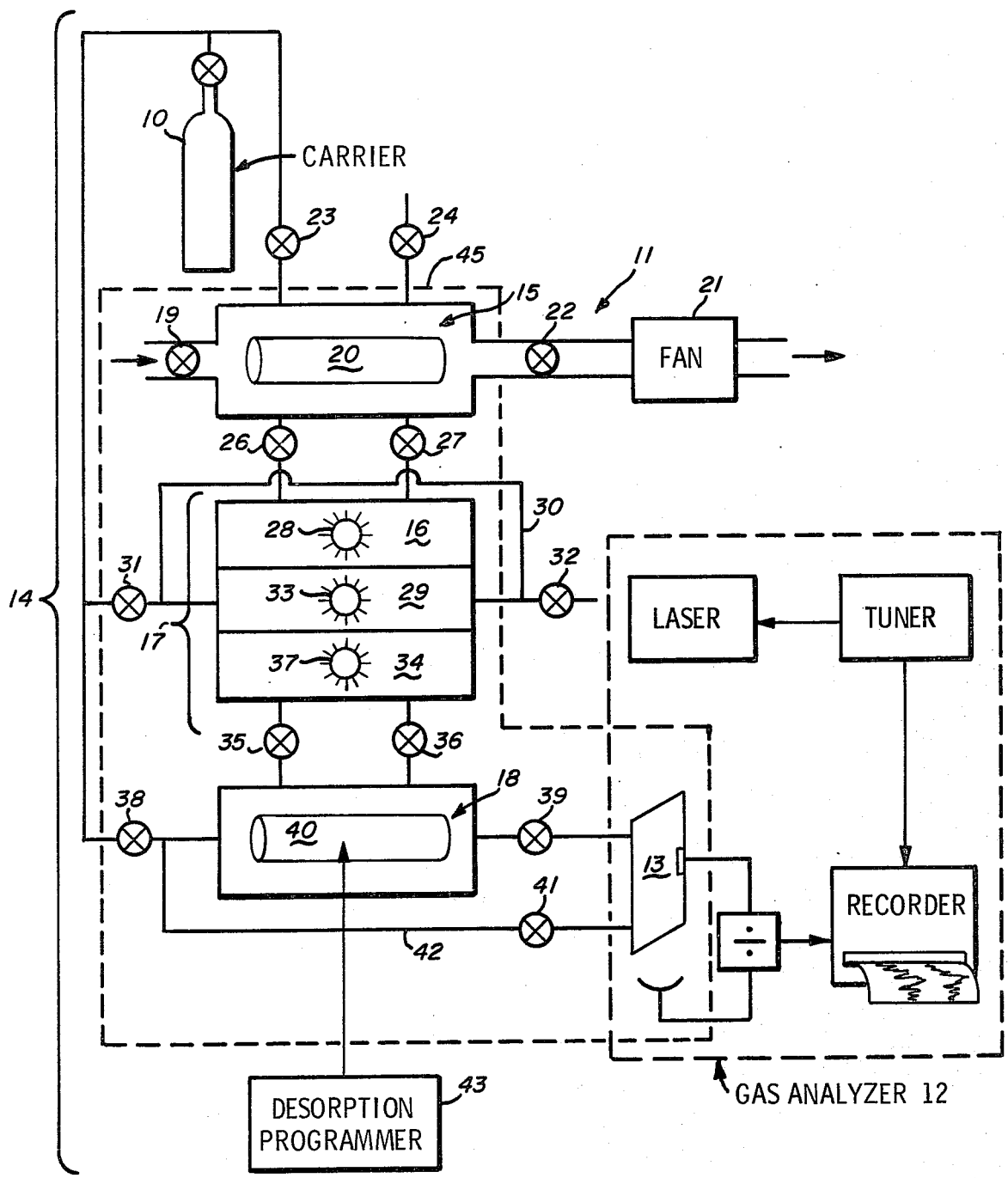

INLET SYSTEM FOR A GAS ANALYZER

BACKGROUND OF THE INVENTION

The present invention relates in general to gas inlet systems for gas analyzers and more particularly to an improved inlet system utilizing the combination for one or more adsorber stages with one or more diffusion membrane stages for greatly increasing the detection sensitivity and selectivity of the detector as regards certain trace quantities of gaseous constituents of interest.

DESCRIPTION OF THE PRIOR ART

Heretofore, bomb detectors have been proposed for identifying the presence of dynamite, for example, in an airplane. The basic method detects the presence of EGDN vapor in air. The essential steps are selective adsorption of the EGDN vapor on a surface, such as a gold surface, thence the timed passage thereof through a short chromatographic partition column, followed by passage through a vapor detector such as an electron capture detector of the type wherein the vapors are ionized. If the vapor of interest has an affinity for electrons it results in a decrease in the electrical conductivity of the gas which is measured. Such bomb detectors are disclosed in U.S. Pat. Nos. 3,430,482 issued Mar. 4, 1969 and 3,568,411 issued March 9, 1971.

One of the problems with this prior art system is the relatively long time taken to make a measurement. For example, a test could be completely run and the system purged for another test in as little as six minutes fifty seconds. Also, another problem with this system is that the gas chromatographic column requires a relatively high degree of maintenance.

It has also been proposed, in connection with laser optoacoustic spectrometers, to provide means for increasing the partial pressure of the gaseous constituent of interest and passing the gaseous constituent of interest at the increased partial pressure through a diffusion membrane into the optoacoustic detector cell of a laser optoacoustic infrared spectrometer for increasing the sensitivity of the spectrometer and removing certain undesired interferences with the desired absorption line. Such interferences are typically associated with water vapor and some of the lighter hydrocarbons which are preferentially excluded from the detector by means of the membrane separator. Such a system is disclosed in U.S. application Ser. No. 643,179 filed Dec. 22, 1975 now issued as U.S. Pat. No. 4,051,372 on Sept. 27, 1977.

One of the problems associated with the use of a membrane separator is that the membrane employs a plasticizer which effuses from the membrane material at very low concentration levels as, for example, at concentration in the parts per billion range. Thus, when a gaseous constituent of interest is in the very low concentration range as of in the parts per trillion range, plasticizers effusing from the membrane are mixed with the relatively heavy hydrocarbons of interest and passed into the detector of the gas analyzer, thereby producing unwanted detection interferences with the gaseous constituent of interest.

SUMMARY OF THE PRESENT INVENTION

The principal object of the present invention is the provision of an improved gas inlet system for use with highly sensitive gas analyzers.

In one feature of the present invention, an adsorbtion type preconcentrator is employed for increasing the partial pressure of the gaseous constituent of interest in a gas mixture to be analyzed. The gaseous constituent of interest, at the increased partial pressure, is then preferentially diffused through a membrane separator and thence into the detector cell of a gas analyzer. In this manner, the partial pressure of the gaseous constituent of interest is raised to a sufficient value prior to the introduction of plasticizers by the membrane so that the interference produced by the plasticizer does not mask detection of the constituent of interest.

In another feature of the present invention, the preconcentrator comprises a metallic adsorber for preferentially adsorbing the gaseous constituent of interest which is thence desorbed from the adsorber into the first stage of the membrane separator.

In another feature of the present invention, the output of the membrane separator is fed into a second adsorber for adsorbing the gaseous constituent of interest which is thence flashed or desorbed into the detector cell of the gas analyzer, whereby the partial pressure differential of the gaseous constituent of interest is maintained at a high value through the membrane separator for increasing the efficiency of the separator for the gaseous constituent of interest. Also by programming the desorption from the adsorber, additional information or selectivity can be achieved.

In another feature of the present invention, the gas analyzer for detecting the gaseous constituent of interest comprises a laser optoacoustic spectrometer.

In another feature of the present invention, the gas inlet system of the present invention is employed in connection with a bomb detector for detecting EGDN vapors emanating from explosives to be found.

Other features and advantages of the present invention will become apparent upon a perusal of the following specification taken in connection with the accompanying drawings wherein:

BRIEF DESCRIPTION OF THE DRAWINGS

The drawing is a schematic diagram, partly in block diagram form, of a gas analyzer system incorporating features of the present invention.

DESCRIPTION OF THE PREFERRED EMBODIMENTS

Referring now to the drawing, there is shown the gas analyzer system 11 incorporating features of the present invention. The gas analyzer system 11 includes an infrared laser optoacoustic spectrometer 12 having an optoacoustic detector cell 13 coupled in gas communication with a source of gas to be analyzed, such as the atmosphere, via the intermediary of a gas inlet system 14. The gas inlet system 14 includes a metallic adsorber type preconcentrator 15, such as that disclosed in the aforecited U.S. Pat. Nos. 3,430,482 or 3,568,411, the disclosures of which are hereby incorporated herein by reference, in their entirety. The output of the preconcentrator 15 is fed to the input or first stage 16 of a two stage membrane separator 17 and thence to the input of a second metallic adsorber concentrator 18, the output of which is fed into the optoacoustic cell 13 of the gas analyzer.

The membrane separator 17 is of the type disclosed in the aforecited U.S. application Ser. No. 643,179, the disclosure of which is hereby incorporated by reference in its entirety, not only for a disclosure of the separator but for a disclosure of the laser optoacoustic respectrometer 12.

More particularly, ambient air to be analyzed is drawn through the adsorber of the adsorber preconcentrator stage 15 via an input valve 19 and an exhaust fan 21. The preconcentrator 15 is connected to the fan 21 via a second valve 22 so that after a sufficient quantity of gas to be analyzed is drawn through the preconcentrator stage 15, valves 19 and 22 are closed and a pair of other valves 23 and 24 are opened to the preconcentrator stage 15 for connection of the preconcentrator stage to a supply 10 of clean permanent gas, carrier gas, such as nitrogen and to permit the clean carrier gas to be flushed through the preconcentrator chamber for removing gaseous constituents not adsorbed upon the adsorber member 20.

After the input preconcentrator stage 15 has been so flushed, valves 23 and 24 are closed and two additional valves 26 and 27 are opened for providing gas communication to the input stage 16 of the membrane separator 17. The adsorber member 20 is then flashed (rapidly heated) from its adsorption temperature, i.e., 10° C. for EGDN vapor, to a temperature sufficient to desorb the adsorbed gaseous constituent of interest. In the case or EGDN vapor, this is a temperature of approximately 80° C. A circulator vane wheel or fan 28 is provided either in the input stage 16 of the membrane separator 17 or in one of the lines interconnecting the preconcentrator stage 15 with input stage 16 of the membrane separator for circulating the desorbed gas from the adsorber stage 15 over and through the input stage 16 of the membrane separator 17.

At the same time that valves 26 and 27 are opened, a second pair of valves 31 and 32 communicating with the intermediate stage 29, of the membrane separator 17, are opened in tubulation 30 interconnecting the two valves externally of the intermediate stage 29 and a second circulator vane or wheel 33 is energized for circulating the gas through the intermediate stage 29 via the tubulation 30. An output stage 34 of the membrane separator 17 is connected to the second concentrator stage 18 via the intermediary of valves 35 and 36.

Valves 35 and 36 are opened at the same time as valves 26, 27, 31 and 32. A circulator 37, provided in fluid communication with the output stage 34 of the membrane separator 17, serves to circulate the gas in the output stage 34 through the second concentrator stage 18. The second concentrator stage 18 is closed off via valves 38 and 39. The gaseous constituent of interest is adsorbed onto the adsorber member 40 of the second preconcentrator stage 18. In a typical example, the valves 26, 27, 31, 32, 35 and 36 are open for only a relatively short time such as, for example, less than 0.5 seconds and preferably the time for the valves to be open would be on the order of the time constant for the diffusion of the gaseous constituent of interest through the particular membrane separator 17. In a typical example where the gaseous constituent of interest is a relatively heavy hydrocarbon, i.e., heavier than propane, and a siloxane membrane material is employed the time constant for diffusion of the heavy hydrocarbon through the separator 17 is on the order of less than 0.5 seconds.

After the time constant diffusion period has expired, valves 35 and 36 are closed and valves 38, 39 and 41 on the output stage of the optpacoustic detector cell are opened and are preferably connected together by means of a return tubulation 42 for circulation of the gaseous material desorbed from the second preconcentrator stage 18 through the optoacoustic detector cell 13 for detection of the gaseous constituent of interest. Detection of the gaseous constituent of interest is obtained by flashing the adsorber member 40 and the desorbed gas is flushed into the detector cell 13 via clean carrier gas. Thereafter, the concentrator stage 18 is closed off from the detector 13 via valves 39 and 41. During detection of the gaseous constituent of interest within the optoacoustic detector cell 13, the membrane separator 17 and the two concentrator stages 15 and 18 are flushed with a clean carrier gas to remove any residual gaseous constituents and the cycle is repeated. Valve 39 is preferably a three-way valve to facilitate flushing. During the flushing phase of the cycle, the adsorbers 20 and 40 are preferably heated to an elevated temperature to assure cleansing, such as 250° C. In addition, after the measurement, the detector cell 13 is flushed with the clean carrier gas, this flushing can occur during the preconcentration phase of the cycle wherein atmosphere is drawn in over the preconcentrator member 20.

In a preferred embodiment, the two preconcentrator stages 15 and 18, membrane separator 17, the optoacoustic detector cell 13 and associated tubes and valves are operated inside an oven 45 at a temperature of approximately 80° C. to inhibit undesired adsorption of gaseous constituents on the inside walls thereof. In addition, the aforecited elements, except for the adsorber members and the membranes are preferably made of glass or quartz to minimize unwanted adsorption thereon.

During the various flushing phases of the cycle, all of the various chambers are opened to a source of clean carrier gas which is exhausted through the various stages of the membrane separator 17, the two concentrator stages 15 and 18, and the optoacoustic cell 13.

In the case of a bomb detector wherein the gaseous constituent of interest is EGDN vapor, the adsorber members in the concentrator stages 15 and 18 are preferably gold and operated at an adsorbing temperature of approximately 10° C. i.e., just above the dew point for the atmosphere, such that water is not unduly adsorbed onto the surface of the adsorber members.

In a typical example, a gold adsorber member 20 of 1000 square centimeter area and a volume of approximately 50 cc. is employed for the input preconcentrator stage 15, and an accumulation time of approximately 10 seconds is used. The membrane separator 17 has two membranes of one to five mil thickness and each with an area of approximately one centimeter and a volume in each of the stages 16, 29 and 34 of approximately 1 cu. centimeter each. With a detector cell 13, having a volume of approximately ten cubic centimeters, the partial pressure of the EGDN vapor is increased over that in the ambient by a factor of approximately 1000 and discrimination against water vapor is obtained by a factor of approximately 1000. In this manner, infrared adsorption interference due to the infrared adsorbtion of water vapor from the IR beam in the detection cell 13 is substantially reduced and other interfering lower weight hydrocarbon constituents are also discriminated against by means of the membrane separator 17. Also, nonpolar hydrocarbon constituents are further separated from the gaseous constituent of interest, when the gaseous constituent of interest is a slightly polar molecule, such as EGDN vapor, by means of the adsorber concentrator stages 15 and 18.

Use of the second concentrator stage 18, located downstream of the membrane separator 17, in addition to reducing the partial pressure on the output stage 34 of the membrane separator for the gas of interest, also permits programmed desorption of adsorbed molecular species by programming the temperature of the adsorbtion member 40 via a programmed heater 43 during the desorption phase of the measurement cycle. This latter feature will permit further separation of gaseous constituents to further aid in their identification by correlating detection in cell 13 with desorption temperature derived from programmed heater 43.

The advantage to the combination to the adsorber preconcentrator 15 in combination with the subsequent membrane separator 17 is that the gaseous constituent of interest is concentrated, i.e., its partial pressure is substantially increased relative to that in the ambient before application thereof to the membrane separator 17 so that heavy hydrocarbon contaminants introduced by the membrane separator are introduced only after the partial pressure of the gaseous constituent of interest has been greatly increased, thereby avoiding unwanted interference therefrom. In this manner the, plasticizers do not interfere with detection of the other heavy hydrocarbons of interest, such as EGDN vapor.

What is claimed is:

1. The method for introducing gaseous material from a source of an initial gaseous mixture of first and second constituents of initial respective partial pressures into a gas analyzer, the steps of:
   adsorbing onto an adsorbtive surface said first gaseous constituent of said mixture for collecting and concentrating said first gaseous constituent on said adsorbtive surface;
   desorbing said adsorbed first gaseous constituent from said adsorbtive surface;
   feeding the desorbed first gaseous constituent to the input of a membrane separator at a partial pressure in excess of said initial partial pressure and diffusing said first gaseous constituent through said membrane separator with a higher value of diffusion conductance than that of the second gaseous constituent of said initial mixture; and
   conducting said desorbed and separated first gaseous constituent of said gas mixture into the detection region of a gas analyzer.

2. The method of claim 1 wherein the step of adsorbing the first gaseous constituent onto an adsorbtive surface comprises the step of adsorbing the first gas constituent onto a metallic adsorbtive surface.

3. The method of claim 2 wherein the metallic adsorbtive surface is gold.

4. The method of claim 1 including the step of:
   adsorbing onto a second adsorbtive surface said first gaseous constituent of said mixture after passage thereof through said membrane separator for reducing the partial pressure on the output stage of the membrane separator for said first gaseous constituent and desorbing said first gaseous constituent from said second adsorbtive surface and conducting said first gaseous constituent as desorbed from said second adsorbtive surface into the detector region of the gas analyzer.

5. In an inlet system for introducing gaseous material from a source of an initial gaseous mixture of first and second constituents at initial respective partial pressures into a gas analyzer:
   adsorber means for adsorbing onto a adsorbtive surface thereof said first gaseous constituent of said mixture;
   membrane separator means having a membrane of the type which has a higher value of diffusion conductance to said first gaseous constituent than to said second gaseous constituent of said gaseous mixture to be analyzed;
   means for desorbing said adsorbed first gaseous constituent from said adsorber means;
   means for conducting said desorbed gaseous constituent, at a partial pressure higher than that of said initial partial pressure of said first gaseous constituent in said initial gaseous mixture, into contact with said membrane separator means so as to conduct said first gaseous constituent through said membrane of said separator means with a higher value of diffusion conductance than that of said second gaseous constituent thereby separating said first and second gaseous constituents; and
   means for conducting said desorbed and separated first gaseous constituent of said gas mixture into the detection region of the gas analyzer.

6. The apparatus of claim 5 wherein said adsorber means comprises a metallic adsorbtive surface.

7. The apparatus of claim 6 wherein the material of said metallic adsorbtive surface is gold.

8. The apparatus of claim 1 wherein said means for desorbing said first gaseous constituent from said adsorber means comprises means for changing the temperature of said adsorbtive surface of said adsorber means for desorbtion of said first gaseous component therefrom.

9. The apparatus of claim 5 including an infrared gas analyzer means having a detector region for detecting the absorption of infrared radiation by the gaseous material conducted from said source via said adsorber means and said membrane separator means into said detector region of said infrared gas analyzer means.

10. The apparatus of claim 9 wherein said infrared gas analyzer means comprises a laser optoacoustic spectrometer means for directing a coherent beam of infrared radiation through the gas to be analyzed within said detector region and wherein the absorption of infrared radiation produces a pressure rise in the gaseous material within said detector region, and including a pressure sensitive detector means for detecting the pressure rise.

11. The apparatus of claim 5 including second adsorber means for adsorbing onto an adsorbtive surface thereof said first gaseous constituent of said mixture, said second adsorber means being disposed in the gas inlet system between said membrane separator means and the detector region of said gas analyzer means.

12. The apparatus of claim 11 including means for desorbing said first gaseous constituent adsorbed onto said second adsorber means and for conducting said desorbed first gaseous constituent into the detector region of the gas analyzer means.

13. The apparatus of claim 12 including program means for programming the desorption of said first gaseous constituent from said adsorbtive surface of said second adsorber means.

* * * * *